United States Patent
Giampapa

Patent Number: 5,201,728
Date of Patent: Apr. 13, 1993

[54] SUBCUTANEOUS IMPLANTABLE MULTIPLE-AGENT DELIVERY SYSTEM

[76] Inventor: Vincent C. Giampapa, 89 Valley Rd., Montclair, N.J. 07042

[21] Appl. No.: 695,107

[22] Filed: May 3, 1991

[51] Int. Cl.⁵ .............................................. A61K 9/22
[52] U.S. Cl. .................... 604/891.1; 424/424; 424/425
[58] Field of Search ............... 604/890.1, 891.1, 892.2; 424/422, 423, 424, 425, 484, 486

[56] References Cited

U.S. PATENT DOCUMENTS

| | | | |
|---|---|---|---|
| 4,511,355 | 4/1985 | Franetzki et al. | 604/131 |
| 4,544,371 | 10/1985 | Dormandy et al. | 604/891.1 |
| 4,596,575 | 6/1986 | Rosenberg et al. | 604/891.1 |
| 4,865,845 | 9/1989 | Eckenhoff et al. | 424/424 |
| 4,886,514 | 12/1989 | Maget | 604/891.1 |
| 4,952,403 | 8/1990 | Vallee et al. | 424/422 |
| 5,030,216 | 7/1991 | Theeuwes et al. | 604/892.1 |
| 5,045,082 | 9/1991 | Ayer et al. | 604/892.1 |
| 5,059,175 | 10/1991 | Hanover et al. | 604/891.1 |
| 5,062,841 | 11/1991 | Siegel | 604/891.1 |
| 5,067,943 | 11/1991 | Burke | 604/141 |
| 5,137,727 | 8/1992 | Eckenhoff | 424/422 |

FOREIGN PATENT DOCUMENTS

| | | | |
|---|---|---|---|
| 3317536 | 11/1984 | Fed. Rep. of Germany | 604/891.1 |
| 2621248 | 4/1989 | France | 604/891.1 |

Primary Examiner—C. Fred Rosenbaum
Assistant Examiner—Mark O. Polutta
Attorney, Agent, or Firm—M. K. Silverman

[57] ABSTRACT

There is provided an implantable multiple-agent delivery system which includes a pod proportioned for subcutaneous implantation beneath the dermis of the skin, the pod including a porous surface having at least one internal chamber there within which is in fluid communication with the porous surface. The system further includes a dome proportioned for complemental, selectable detachable securement upon the pod. The dome includes a plurality of interior chambers, each in fluid communication with the internal chambers of the pod. Bio-acting agents, such as hormones, biologic response modifiers, free radical scavengers, and other therapeutic agents may be provided, within the chambers of the dome, prior to implantation. Such agents with the chambers of the dome will, through the use of time release microelectronics, enter at least one of the interior chambers of the pod for transmission, through the porous surfaces thereof, into a growth factor stimulated capillary matrix and then to the bloodstream of the user. The pod may be removed, refilled, and resecured to the dome upon exhaustion of its contents or upon medical requirement for changes in medication. The surface of the pod may be treated with one or vascular growth factors or related biologic molecules.

5 Claims, 2 Drawing Sheets

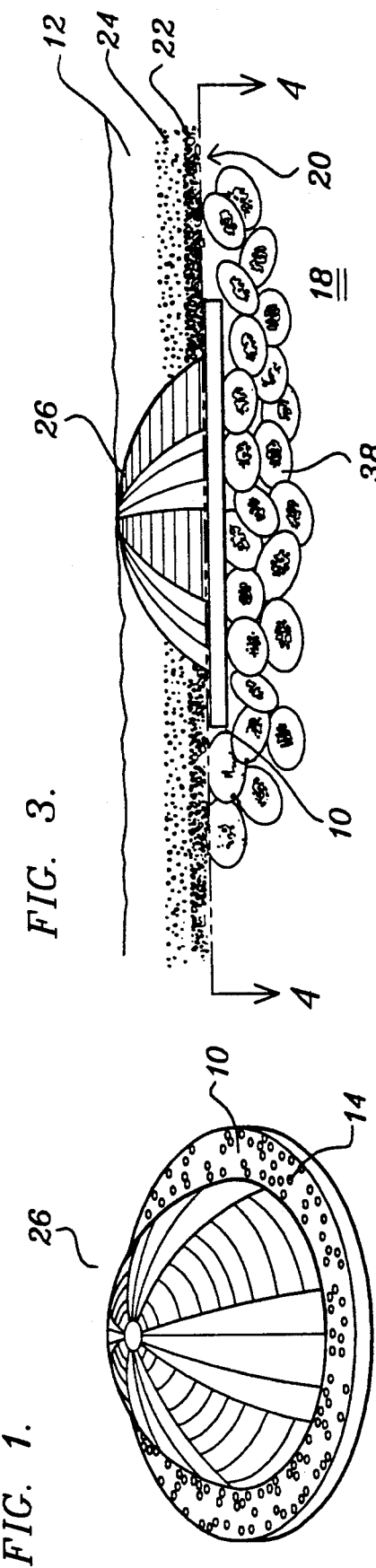
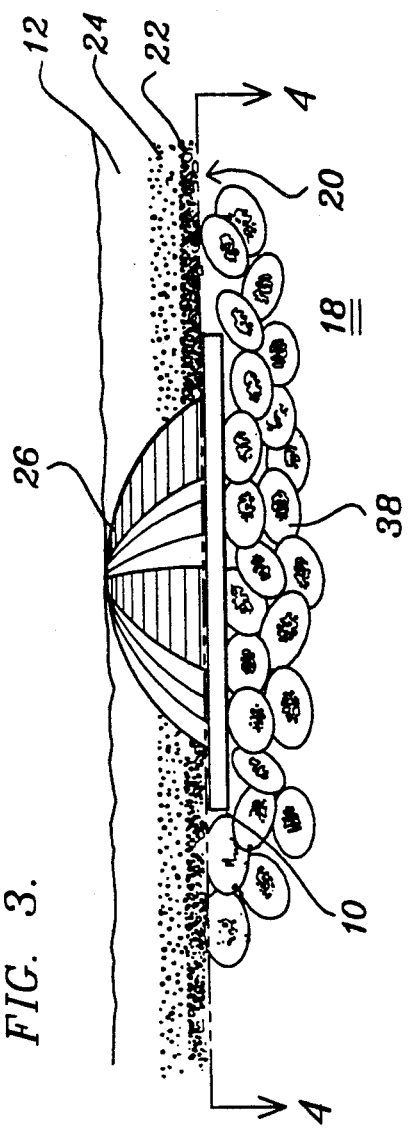
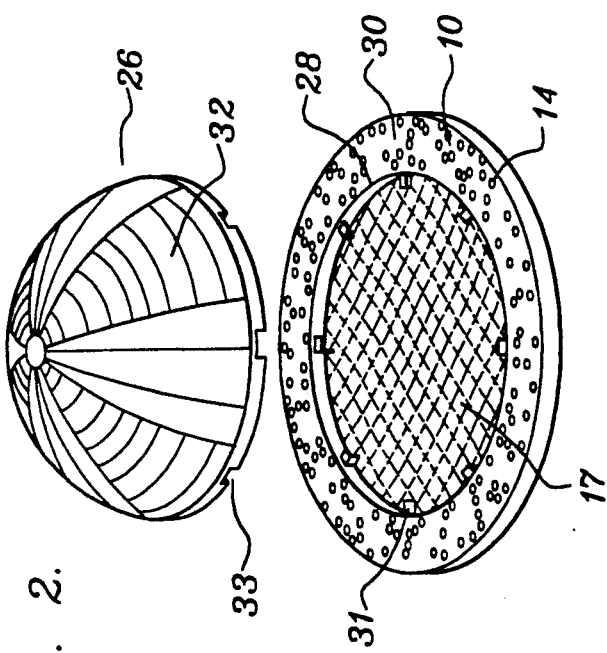
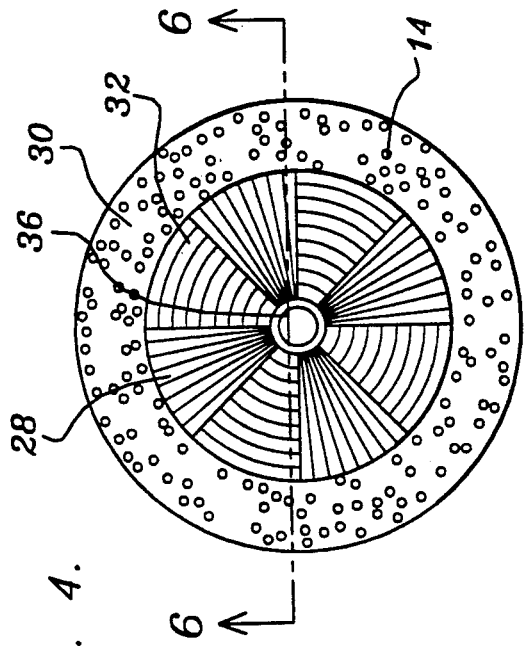

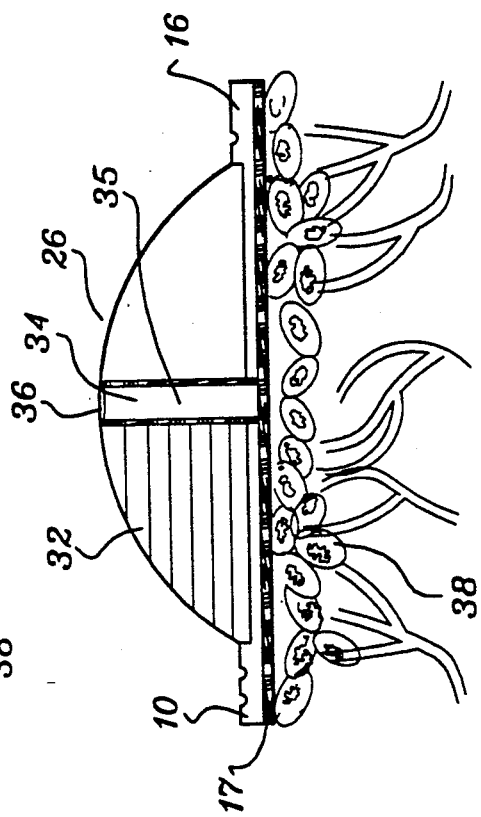
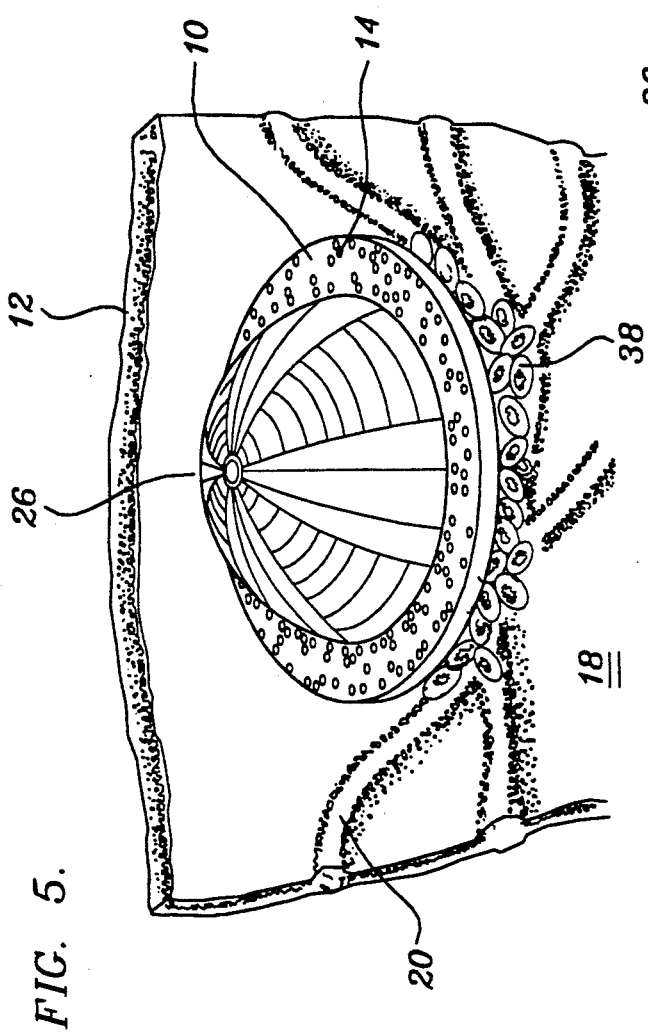
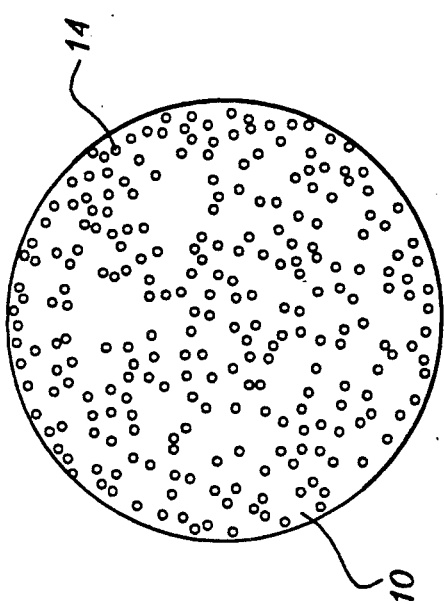

SUBCUTANEOUS IMPLANTABLE MULTIPLE-AGENT DELIVERY SYSTEM

BACKGROUND OF THE INVENTION

The present invention relates to the field of implantable vascular prosthetic device, more particularly, to subcutaneous implant for integration into the vascular/capillary system of a patient for purposes of selectable dispensing, over an extended period of time, of pharmacologic and other bio-acting agents.

A problem which has developed in contemporary pharmacology and areas of bioengineering is that many bio-acting molecules resultant from such efforts are of a size, length, weight and complexity such that they are subject to attack by the enzymatic processes within the digestive tract when such drugs or bio-engineered agents are taken enternally (orally). Further, the state-of-the-art of encapsulation and matrixing of drugs to minimize the effect of digestive tract acids, and to extend the release period thereof are, generally, limited to a number of hours in the resultant effective time period of release of such agents.

Recognizing the above limitations of orally delivered bio-acting agents, and realizing the limitations of drug delivery by means of hypodermic injection, a number of approaches, by way of implantable micro-infusion pumps/dispensers has appeared in the art. More particularly, such micro-pump and micro-dispensing systems have included electro-chemical means, piezo-electric means, osmotic means, of both an active and passive nature, and miniaturized classical electro-mechanical delivery means. All of these technologies have, as their goal, the provision of extended time-release of drugs and other bio-active substances directly into the bloodstream of the patient. For example, U.S. Pat. No. 4,886,514 to Maget relates to an implantable, electrochemically driven drug dispenser capable of achieving dispensing rates in the range of 0.01 ml per hour to as low as 0.001 ml (one microliter) per hour.

Implantable piezo-electric systems, intended for long-term dispensing of bio-acting agents are represented by U.S. Pat. Nos. 4,938,742 to Smits and 4,944,659 to Labbe. These technologies are entirely solid state and, therefore, are, in principle, capable of unlimited miniaturization and to control thereof by purely electronic means. Thereby, long term, low quantity delivery systems should be achievable by such means.

The category of so-called active osmotic pumps is represented by U.S. Pat. No. 4,898,582 to Faste which employs chemo-mechanical processes which do not require any source of electrical energy, such as a battery. In this technology, a membrane is reciprocated responsive to a chemical reaction to, over extended periods of time, provide controlled, long-term release of bio-acting substances.

So-called passive osmotic pump systems have appeared for use in both oral and have been suggested for subcutaneous delivery systems. Such pumps, which often involve the use of lipids, are represented by U.S. Pat. Nos. 4,111,201 to Theeuwes; No. 4,439,196 to Higuchi; and No. 4,685,918 to Amidon et al. Passive osmotic pumps make use of a rigid enclosure having an expandable compartment which over time, supplies pressure against an adjacent second compartment to effect pressure gradient against the wall of the second compartment such that, over prolonged period of time, a bio-acting agent within the second compartment will be forced across an aperture in the rigid enclosure and into the bloodstream or tissue of the patient. Such systems of osmotic drug delivery an address of drug delivery rates of picoliters per hour, that is, billions of liters per hour. Accordingly, it is believed that extremely low quantity and prolonged delivery rates are achievable through the use of such osmotic systems. Nonetheless, such approaches do not address the needs of the patient or user having, as is often the case, the requirement for a timed, sequenced, and/or pulsed delivery of a number of different bio-acting agents, often known as biologic response modifiers. Also, little is known regarding the long term effect of osmotic systems, when such systems are with subcutaneous implants.

A further concern in the area of implantable delivery systems is the ability of the vascular system to provide sufficient volume, rate, and pressure of blood flow to the delivery means in order to enable the bio-acting agents to enter the bloodstream on a reliable basis. Two approaches to this problem have appeared in the art. One is the approach of Powell, (see U.S. Pat. No. 4,929,442) of providing an improved physiological carrier to permit the particular bio-acting agent to become more effectively transferred to the bloodstream. A second approach to the problem of access of the agents to the vascular system is reflected in U.S. Pat. No. 4,820,626 (1989) to Williams et al, which is concerned with methods of treating the surface of subcutaneous implants with microvascular endothelial cells to better integrate the implant into the vascular system of the patient to achieve better bloodflow to the dispensed agents.

The instant invention is an improvement of the said technology of Williams in that use is made of one or more of a combination of so-called vascular growth factors which communicate directly with the so-called angiogenesis gene which, it is believed, is the basis of all human vascular development. Accordingly, through the use of growth factors, and related biological molecules which have been recently discovered, vascular growth, of capillaries, veins, and the like, upon the surface of an implant can be stimulated. This has been demonstrated by Ogawa, and others, who has placed a vascular growth factor within an osmotic pump capsule, subcutaneously implanted the same, thereby, stimulated the growth of capillaries and related vascular materials which are identified with vascular growth and development.

Also there has appeared in the art such materials as polytetrafluoroethylene having specially configured fibers, fibrils and other structures adapted for vascular implantation. Accordingly, a combination of synthetic and organic materials have appeared in recent years, which in one fashion or another, stimulate vascular growth and/or activity.

The instant invention builds upon the above advances in molecular biology and microelectronics. It more particularly provides for a selectably detachable component of a dispensing system in which a permanently implanted vascular portion of the system cooperates with a replaceable component thereof within which various biologic response modifiers, and other, agents may be provided and dispensed at low rates and for prolonged periods into the implanted vascular portion and therefrom into the human body.

SUMMARY OF THE INVENTION

There is provided an implantable multiple-agent delivery system which includes a pod proportioned for subcutaneous implantation beneath the dermis of the skin, said pod comprising a porous surface and having at least one internal chamber there within which is in fluid communication with said porous surface. The system further includes a dome proportioned for complemental, selectable detachable securement upon said pod, the dome comprising a plurality of interior chamber, each having fluid communication with said internal chambers of said pod. Bio-acting agents, such as hormones, biologic response modifiers, free radical scavengers, and other therapeutic agents may be provided, within the chambers of said dome, prior to implantation. Each of said chambers will, through the use of time release means, enter at least one of said interior chambers of said pod for release, through the porous surfaces thereof, into the stimulated vascular matrix and into the bloodstream of the user. Said dome may be removed, refilled, and resecured to said dome upon exhaustion of its contents or upon medical requirement for changes in medication. The surface of said pod may be treated with one or more vascular growth factors or related biologic molecules.

It is accordingly an object of the present invention to provide a subcutaneous vascular implant for purposes of extended time release delivery of a plurality of bio-acting agents.

It is another object of the present invention to provide a vascular implant having a component thereof which may be selectably removed, refilled with medication, and resecured to a permanently implanted vascular portion of the system.

It is a further object cf the present invention to provide a means in nature of a prosthetic gland from which needed hormones, related agents and combinations and can, over a prolonged period of time, be released into the bloodstream.

The above and yet other objects and advantages of the present invention will become apparent from the hereinafter set forth Detailed Description of the Invention, Brief Description of the Drawings, and Claims appended herewith.

BRIEF DESCRIPTION OF THE DRAWINGS

FIG. 1 is a perspective, schematic view of the inventive system prior to implantation.

FIG. 2 is an exploded view of the system.

FIG. 3 is a side conceptual view of the system after implantation.

FIG. 4 is a top cut-away view of the internal compartments of the dome, taken along Line 4—4 of FIG. 3.

FIG. 5 is a perspective conceptual view of the system implanted within the dermis.

FIG. 6 is a cross-sectional view of FIG. 1, taken along Line 6—6 of FIG. 1.

FIG. 7 is a bottom view of the inventive system.

DETAILED DESCRIPTION OF THE INVENTION

With reference to FIGS. 1 and 2, the inventive system may be seen to include a pod 10 having a diameter preferably in the range of 1 to 3 centimeters. As such, it is proportioned for subcutaneous implantation beneath the epidermis 12 and dermis 22 see FIGS. 3 and 5. The surface of pod 10 contains a multiplicity of pores 14 and, as well, at least on internal chambers 16 which, through fluid transfer means 17, such as a capillary mesh, is in fluid communication with said pores 14. The walls of pod 10 are formed of a porous silicone or polytetraflorothylene to permit ease of ingrowth of capillaries within tissue layer 18 and at subcutaneous border 20.

In a preferred embodiment, the porous surface of pod 10 is treated with one or more vascular growth factors, or related biologically active materials which operate to communicate directly with the angiogenesis genes of nearly cells which, it is believed, are responsible for all vascular development. Accordingly, growth factors and the like may be viewed as genetic "receivers" while the angiogenesis genes operate as a genetic transmitter. A number of vascular growth factors have been identified. These are vascular endothelial growth factor (VEGF), platelet derived growth factor (PDGF), vascular permeability growth factor (VPF), basic fibroblast growth factor (bFGF), and transforming growth factor beta (TGF-$\beta$). Related molecules which operate in a similar fashion may also be used. These are known cytokines and gangliosides.

The use of endothelial cells upon the surface of a prosthetic device, employed in the context of vascular surgery, is known as is taught in U.S. Pat. No. 4,820,626 (1989) to Williams et al entitled *A Method of Treating a Synthetic or Naturally Occurring Surface with Microvascular Endothelial Cells*. Instant invention, however, does not relate to the use of a growth factor treated surface in the context of a surgical device or system. Rather, said pod 10 operates as a permanently implanted component of a long term multi-agent drug delivery system. Its effectiveness is maximized by reason of its placement at the subcutaneous border 20 of the patient, this constituting the location of greatest blood flow. As such, it is an ideal location for any agent dispensing device which relies, for its efficacy, upon permanent access to a relatively consistent of level of blood flow. As may be noted in FIG. 3, the subcutaneous border 20 is defined by the interface between dermis 22 and tissue layer 18. Between dermis 22 and epidermis 12 is the dermal layer known as stratum germinativium 24.

It is established in the literature that capillary growth may be artificially generated through the implantation of vascular growth factors upon the surface of an implant. See for example, Ogawa et al, "Transforming Growth Factors Beta One and Beta Two Induce Synthesis and Accumulation of Hyluronate and Chondroitin Sulphate In-Vivo", 3 *Growth Factors* 53–62 (1990). Further, the medical literature concerning growth factors contains over 200 papers on the subject of vascular growth factors published between 1989 and early 1991. Accordingly, the technology of the use of vascular growth factors to stimulate artificial capillary growth is known in the art.

The present drug delivery system further includes a dome 26 (see all figures) which is proportioned for complemental, detachable securement on top of pod 10 and, more particularly, within the inner circumference 28 of annular region 30 of the pod 10. Said dome 26 and pod 10 may be secured through the use of bayonnet lock elements 31 and 33 of the type shown in the exploded view of FIG. 2.

As may be noted in the radial cross-sectional view of FIG. 6, the interior of dome 26 comprises a plurality of interior chambers 32 each having fluid communication with fluid transfer means 17 of said interior chamber 16 of pod 10. Also shown in FIG. 6 are vertical fluid transfer means 33 which communicate with said mean 17.

As may be noted in the view of FIG. 3, the top of dome 26 will reach through dermis 22 and will stop at epidermis layer 12.

In another embodiment, the top of dome 26 may protrude above epidermis 12 in the manner taught in U.S. Pat. No. 4,552,561 (1985) to Eckenhoff, entitled *Body Mount Pump* which teaches the use of an implantable pump having a transparent top through which the contents of the dome portion may be seen.

In either embodiment, an essential concept relative to the instant invention is that a plurality of bio-acting agents may be placed within compartments 32 of dome 26 and, after their exhaustion, or upon the election of the physician, dome 26 may, through minor out-patient surgery, be removed from pod 10, refilled, and then re-secured to pod 10.

With reference to FIG. 4, the various radial and polar segments shown within compartments 32 of dome 26 are shown to represent the time release aspect associated with the bio-acting agents within the compartments 32 of dome 26. More particularly, any one or more, either singularly or in combination, of the technologies discussed in the Background of the Invention may be employed to effect time release of the bio-acting agents through vertical fluid transfer means 36 (see FIG. 6) to inner chamber 16 of pod 10 and, thereby, through pores 14 of tall sides of he pod and into the blood at subcutaneous border 20.

The potential technologies for effecting extended duration time release run the gamut from substantially passive means such as osmotic pumps to electrochemically driven drug dispensing means (see Maget, discussed in the Background of the Invention), to systems requiring use of a battery 36 (see FIG. 4 and 6) acting as a source of low level power to a piezo-electric micro pump and micro valves, such valves operating within chambers 32 of dome 26, as is generally taught in the references to Smits and Labbe, discussed in the Background of the Invention. Such solid state piezo-electric means are particularly suitable where small rates of release, e.g., nanoliters per hour, over a period of months, is required.

The instant invention may also be practiced through the use of relatively crude subcutaneous implant devices such as that reflected in U.S. Pat. No. 3,443,561 (1960) Reed, entitled *Subcutaneous Implant Device*, previously used in veterinary applications, as the pod 10 of the present system. Accordingly, long known implants of the type of Reed may be equipped with a dome, as above described, to thereby provide for an extended time release capability of a plurality of a bio-acting agents.

In broad concept the instant invention may be viewed as a prosthetic gland in that, through its operation, a sustained release of hormones of various types, including, human growth factors designed to increase muscle mass, decrease body fat deposition, and stimulate immunological responses, may be employed. More generally, such hormones are known as biologic response modifiers and, generally relate to those classes of agents which have been determined to be associated with the aging process or immune system. More particularly, the absence or decrease of hormones and/or their growth factors as well as free radical scavengers have been identified as a primary cause of the aging process. To use the above transmitter/receiver analogy, the operation of the human gene may be compared to that of a transmitter, while the operation of growth factors and related molecules may be viewed as genetic receivers or receptors. In other words, the aging process is now believed to be the result of a failure in one or more of the genetic processes of transmission and reception of genetic information. The avenues by which genetic instructions travel from genes to growth factors is often termed the enzymatic pathways. More particularly, certain enzymes are associated with the operation of so-called messenger DNA which communicates genetic instructions from the gene to the growth factor where the instructions of the gene are then executed in the particular tissue with which that growth factor is associated. Growth factors or hormone regulated processes, which affect of an enzymatic pathway may be purely local to the cell (an autocrine pathway) or the genetic instruction may be delivered at a considerable biological distance (an endocrine pathway).

In that genetic research has, as yet, been unable to locate any so-called aging gene, it is believed that most manifestations of the aging process occur as a result of breakdown in either or both the enzymatic pathways or of the actual growth factors which to execute the genetic instructions. More particularly, in vitro experiments have shown that most genes have the capability of reproducing tens of thousands of times this corresponding to what would relate to dozens of normal lifespan specie generations. It is therefore now believed, that most aspects of aging are a result of the inability of cell classes within tissues to continue to execute genetic instructions, that is, it is now widely believed that aging, as it is presently understood, is primarily a result of the failure of cells to carry out essential genetic instructions from genes which, in and of themselves, appear to be capable of functioning indefinitely.

As a more modest goal of what has become known as growth factor therapy, certain diseases which cause a more dramatic manifestations of the aging process can, through the system of the present invention, be directly treated. For example, osteoporosis which is directly related to growth hormone deficiency can be treated; similarly, certain areas of the skin and related fat deposits which are generally associated with aging, may be treated through the use of epidermal growth factors which have been identified including the above mentioned fibroblast growth factor (bFGF) which is generally associated with the growth of muscle mass.

Further, one popular theory of aging is the process known as glycolysolation in which certain compounds causes a cross linking of certain proteins thereby rendering the above referred to enzymatic pathways less sufficient. Accordingly, through the use of hormones and other molecules, such as free radical scavengers, such cross linking or glycolysolation of proteins necessary for healthy enzymatic pathways, can be effectively eliminated.

The important role of growth factors in combating diseases, such as carcinomas and anti-viral diseases, is recognized by Powell, in U.S. Pat. No. 4,929,442 (1990) (see Background of the Invention). He discusses the importance of glycoproteins and growth factors in the combating of certain topical and subcutaneous conditions. Further, Powell teaches a physiologically acceptable carrier which in the instant invention and, more particularly, within the chamber of dome 26, may be employed to increase the effectiveness of other bio-acting agents which may be employed within the scope of the present invention. Further, through the use of vascular growth factors in at least one of the chambers 32 of dome 26, the vascular growth factor applied to pores 14 at the surface of pod 10 will co-act to provide long term "nourishment" to the vascular growth factors applied to the surface of pod 10 and to the artificially created capillary growth (see FIG. 5) within tissue 18.

Persons suffering from high cholesterol may be effectively treated through the use of Lovastatin and other anti-cholesterol drugs which are more effective when delivered in small quantities over an extended period of time. Further, even persons having a normal cholesterol level can benefit from the use of such anti-cholesterol agents to decrease age related arterial damage as well as to provide improved oxygenation to the entire central nervous system as well as to other vital organs. Accordingly, within the scope of the present invention, it is anticipated that persons not considered ill by earlier medical standards, will be able to make advantageous use of the instant system.

Further, there exists numerous medical therapies in which one drug or drug system is optimally employed in combination with a second or many other drugs such that a desired synergistic effect can be achieved. For example, U.S. Pat. No. 4,971,951 (1990) to Garcia y Bellon et al, teaches a therapy known as Insulin Potentiation Therapy which has application to numerous diseases. In the practice of Insulin Potentiation Therapy the effect of the particular therapeutic or bio-acting agent is potentiated by the parental injection to the patient, approximately 20 minutes prior to the administration of the therapeutic agent, of a prescribed dosage of insulin. In other words, the action of the therapeutic or bio-acting agent of interest is potentiated, within the intracellular compartment, that is, the permeability to cross the cell membrane is enhanced, by a "pulse" of insulin at a prescribed time prior to the administration of the therapeutic agent, (which in the case of insulin potentiation therapy involves the combination of glucose or dextrose with the therapeutic agent) must occur. As such, the present system will be particularly useful in that one compartment 32 within dome 26 may contain a material such as insulin which, through the use of electronic means as is taught in the references to Smits supra and others, may be pulsed into the subcutaneous border 20 at a programmed period of time prior to pulsing from one or more other compartments of dome 32 occurs.

More generally, through the instant invention, a physician such as endocrinologist may prescribe a number of hormonal, therapeutic and other bio-acting products having a variety of different volumetric, molaric and temporal time release specifications. Further, the respective compartments 32 of dome 26 may be equipped with any of a variety of biological sensors such that the electrical, chemical or mechanical delivery means, as the case may be, are initiated in response to a particular indication which may be monitored through blood flow in tissue 18 within the region of said artificially stimulated capillary ingrowth 38.

It is to be further appreciated that, within the scope of the present invention, compartments 32 of dome 26 may be provided with pre-packaged time release elements such as bio-acting materials contained within silicone tubules as a presently are manufactured and sold by the Leiras Medical Corporation of Helsinki, Finland. A number of such implantable tubules now exist for the release of birth control acting hormones. However, such tubules may be equipped with other hormones, therapeutic agents and the like as above discussed, and the geometry thereof adapted for implantation within the polar and radial segments of compartments 32 of the dome 26.

Accordingly, while there has been shown and described of the preferred embodiment of the present invention it is to be appreciated that the invention may be embodied otherwise than is here and specifically shown and described and, within said embodiment, certain changes may be made within the form and arrangement of the parts without departing of the underlying principles of this invention as set forth in the Claims appended herewith.

Having thus described my invention what I claim as new, useful and non-obvious and, accordingly, secured by Letters Patent of the United States is:

1. A subcutaneously implantably, multi-agent delivery system, comprising:
   (a) a pod for subcutaneous implantation beneath the dermis of the human body, said pod comprising a porous surface between an interior and exterior thereof and, further comprising, fluid transfer means in fluid communication with said porous surface, said pod having an opening at the top thereof, said pod formed of a bio-compatible material, said porous surface between said interior and exterior of said pod provided with one or more vascular growth factors to promote growth of blood capillaries into and about said porous surface of said pod;
   (b) a dome portioned for complemental detachable securement within said opening of said pod, said dome including at least one chamber having selectable fluid communication with said fluid transfer means of said pod, in which bio-acting materials may be stored within said chamber of said dome prior to implantation, said dome formed of a biocompatible material, attached to said pod; and
   (c) time dependent material release means interfaced between said chamber of said dome and said fluid transfer means of said pod,
   whereby said bio-acting materials are controllably released from said chamber of said dome, into said pod and, therefrom, through said porous surface into the bloodstream, in which said dome, after exhaustion of the materials therewithin, may be removed, refilled and re-secured to said pod.

2. The system as recited in claim 1 which said vascular growth factors are selected from the group of growth factors consisting of vascular endothelial growth factor, platelet growth factor, vascular permeability factor, basic fibroblast growth factor and transforming growth factor beta,.

3. The system as recited in claim 1 in which said pod is formed of a silastic material having a porous vascular ingrowth characteristic.

4. The system as recited in claim 3 in which said silastic material is selected from the group consisting of silicone and polytetrafluorethylene.

5. The system as recited in claim 1, in which said material release means is situated within an axial central core of said dome.

* * * * *